(12) United States Patent
Ding et al.

(10) Patent No.: US 12,257,580 B2
(45) Date of Patent: Mar. 25, 2025

(54) MICROFLUIDIC CHIP AND MANUFACTURE METHOD THEREOF, AND CELL SEPARATION AND SINGLE-CELL WESTERN BLOTTING METHOD

(71) Applicant: Water Bear Health Technology (Nantong) Co., LTD., Nantong (CN)

(72) Inventors: Xianting Ding, Shanghai (CN); Ainur Abula, Shanghai (CN); Ting Zhang, Shanghai (CN); Haiyang Xie, Shanghai (CN)

(73) Assignee: Water Bear Health Technology (Nantong) Co., LTD., Nantong (CN)

( * ) Notice: Subject to any disclaimer, the term of this patent is extended or adjusted under 35 U.S.C. 154(b) by 475 days.

(21) Appl. No.: 17/490,716

(22) Filed: Sep. 30, 2021

(65) Prior Publication Data
US 2023/0102204 A1    Mar. 30, 2023

(51) Int. Cl.
*B01L 3/00* (2006.01)
*G01N 33/53* (2006.01)
*G01N 33/68* (2006.01)

(52) U.S. Cl.
CPC ... *B01L 3/502753* (2013.01); *B01L 3/502707* (2013.01); *B01L 3/502715* (2013.01);
(Continued)

(58) Field of Classification Search
None
See application file for complete search history.

(56) References Cited

U.S. PATENT DOCUMENTS

2020/0299672 A1* 9/2020 Spuhler ............. B01L 3/502761
2021/0114029 A1* 4/2021 Yellen ................... C12M 23/16

FOREIGN PATENT DOCUMENTS

CN    107746794 A  *  3/2018  .......... B01L 3/50273

OTHER PUBLICATIONS

Zheng et al., 3D microfilter device for viable circulating tumor cell (CTC) enrichment from blood, Biomed Microdevices. Feb. 2011; 13(1) (Year: 2011).*

(Continued)

*Primary Examiner* — Paul S Hyun
*Assistant Examiner* — Mickey Huang
(74) *Attorney, Agent, or Firm* — FITCH, EVEN, TABIN & FLANNERY LLP

(57) ABSTRACT

A microfluidic chip comprises: a first unit which has a channel for a cell sample to pass through and is configured to separate circulating tumor cells in the cell sample; a second unit, a front end of which communicates with a tail end of the first unit, and the second unit is configured to capture single cells from the separated circulating tumor cells and subject the captured single cells to closed lysis; and a gel layer which is provided at the second unit. The microfluidic chip is configured to implement the binding of a protein molecule of the single cell with an antibody in the gel layer after the single cell is lysed. A cell separation and western blotting method using the microfluidic chip comprises: lysing circulating tumor cells, capturing, and implementing the binding of a lysate with an antibody. A manufacture method of the microfluidic chip, comprises: manufacturing a first interlayer and a separation unit; manufacturing a second interlayer and pasting the second interlayer on a basal layer, and manufacturing a single-cell capture unit; and bonding the first interlayer with the separation unit and the second interlayer with the single-cell capture unit.

17 Claims, 6 Drawing Sheets

(52) U.S. Cl.
CPC ......... *G01N 33/5304* (2013.01); *G01N 33/68* (2013.01); *B01L 2200/12* (2013.01); *B01L 2300/0663* (2013.01); *B01L 2300/0681* (2013.01); *B01L 2300/0819* (2013.01); *B01L 2300/0883* (2013.01); *B01L 2300/0887* (2013.01)

(56) References Cited

OTHER PUBLICATIONS

Ayinuer et al., CN1077469794 A translated Abstract, 2018, Patent published by CNIPA, translation provided by Espacenet (Year: 2018).*

Liu, Xiao, et al.; "Epithelial-type systemic breast carcinoma cells with a restricted mesenchymal transition are a major source of metastasis."; Science Advances; vol. 5.6; Jun. 19, 2019.

* cited by examiner

MICROFLUIDIC CHIP AND MANUFACTURE METHOD THEREOF, AND CELL SEPARATION AND SINGLE-CELL WESTERN BLOTTING METHOD

FIELD OF THE INVENTION

This application relates to the field of circulating tumor cell separation and protein analysis, and in particular to a microfluidic chip and a manufacture method thereof, and a circulating tumor cell separation and single-cell western blotting method using the microfluidic chip.

DESCRIPTION OF THE PRIOR ART

Circulating Tumor Cell (CTC)

With the improvement of people's life quality and the extension of people's lifespan, the mortality associated with cancer has steadily increased in the past few decades, and cancer has become the "number one killer" for human beings. A study conducted by the World Health Organization shows that, if a cancer patient can be identified and treated before metastasis occurs, at least 30% of death can be prevented. Circulating tumor cells (CTCs) in blood are one of the main culprits that cause the distant metastasis of a tumor with the blood circulatory system and the death of a patient with the tumor. CTCs refer to tumor cells that fall off from a solid tumor (primary tumor or metastasis) spontaneously or due to diagnosis and treatment operations, and then infiltrate into the blood circulation. Most CTCs undergo apoptosis or are phagocytized after re-entering the peripheral blood. A small number of CTCs can evade the body's immunity and reside in the primary or distant organ, thereby causing recurrence or metastasis. The circulating tumor cell is one of the few new tumor molecular markers that have been researched and used in the past 30 years. The number and protein expression of CTCs can be detected to diagnose a tumor, determine a prognosis, and monitor a therapeutic effect. For example, the epithelial-mesenchymal transition (EMT) and epithelial cell adhesion molecule over-expression of CTCs often suggest poor prognosis of a tumor patient; and the number of CTCs in blood after surgery or radiotherapy can be compared with that before the surgery or radiotherapy to determine whether the treatment is effective, which has important clinical research and practice values.

Circulating Tumor Cell Heterogeneity

Cell heterogeneity is a ubiquitous biological phenomenon, which is often observed in cell physiological processes such as stem cell differentiation, embryonic development, tumorigenesis, drug working, and immune response. Even cells that look the same apparently may have significant heterogeneity. In the field of circulating tumor cell research, researchers have gradually realized that solving the problem of cell heterogeneity is the key to clinical translational research of research results. circulating tumor cells and disseminated tumor cells (DTCs) are considered to be the "seeds" that cause distant metastasis of tumors. Heterogeneity of CTCs and DTCs, dynamic regulation of EMT, and subgroups with high metastatic potential are some research hotspots at present.

A large number of studies have shown that CTCs exist in the peripheral blood in different forms, including free single CTCs and aggregated cell masses. In addition, tumor cells undergo different levels of epithelial-mesenchymal transition when entering the peripheral blood circulation, and thus there are different types of CTCs, including epithelial phenotype, mesenchymal phenotype, and hybrid epithelial/mesenchymal phenotype. On Jun. 20, 2019, the following research result of Wang Hongxia's team from Shanghai First People's Hospital was published online by the Science Advances: "Epithelial-type systemic breast carcinoma cells with arestricted mesenchymal transition are a major source of metastasis". Studies have shown that EMT of tumor cells will not definitely lead to a full epithelial or mesenchymal state, and many tumor cells are in an intermediate state of EMT, showing heterogeneity. Compared with mesenchymal phenotype cells (M, M/E), a cell subtype dominated by epithelial phenotype cells (E and E/M) has stronger metastatic potential. EPCAM+CTCs and DTCs are significantly related to distant metastasis and poor prognosis. In the studies, the EMT heterogeneity of CTCs is revealed through morphological, molecular, and phenotypic analysis, which confirms the coexistence of epithelial and mesenchymal characteristics of CTCs. In addition, tumor cells themselves show high heterogeneity. As one of the characteristics of tumors, tumor heterogeneity is the root cause of differences in malignant growth, invasion and metastasis, drug susceptibility, and prognosis of tumors.

Therefore, the targeted therapy of cancer needs to provide quantitative and highly-specific target protein detection at a single-cell resolution level. The study on cell heterogeneity can provide rich and key genetic expression information for individualized treatment, and lay a foundation for the formulation of treatment plans and the selection and development of targeted drugs.

Circulating Tumor Cell Separation

More diagnostic information and treatment information can be obtained through CTC analysis, which can more effectively help find early tumor metastasis, evaluate the prognosis of a tumor patient, and determine a therapeutic effect of individualized treatment. Real-time dynamic analysis of CTC characteristics of a tumor patient will provide a new basis for true individualized treatment of a cancer patient. A CTC content in the peripheral blood is extremely low, where per 10 ml of blood, there may be only one to dozens of CTCs, but there are 100 million of white blood cells and 50 billion of red blood cells. Therefore, in order to achieve CTC analysis, CTCs must be separated first.

With the development of flow cytometry, microfluidic technology, and nanotechnology, separation techniques for CTCs show a trend of convergence, which greatly improves the sensitivity and specificity of CTC separation. Separation techniques can be divided into two categories based on principles: immunological methods and physical methods. Immunological methods are distinguished according to molecular markers on the surface of CTCs, including immunomagnetic bead method and affinity ligand method. However, the above methods have many problems. For example, not all tumors are derived from epithelial cells, and even tumors derived from epithelial cells may gradually lose epithelial markers, which can be seen from the application limitations of the CellSearch system. The physical methods are based on the differences of a size and a density of CTCs from a size and a density of other cells in blood, including sorting method based on inertial force, filtration method, sonic sorting method, dielectrophoresis sorting method, lateral flow sorting method, and the like.

Circulating Tumor Cell (CTC) Analysis

As a new non-invasive cancer surveillance technology with high feasibility and reproducibility, CTC can truly participate in the detection, medication guidance, prognostic evaluation, and the like of a tumor throughout a disease course, which will greatly promote the precise treatment of the tumor. The study on CTC heterogeneity is at the single-cell resolution level, because the heterogeneity among single cells exists at a DNA level, an RNA level, a protein level, and the like. In recent years, technical means for the research on CTC characteristics mainly include gene sequencing, transcriptome sequencing, multi-throughput qPCR, immunofluorescence in situ hybridization, and the like.

However, related research results in transcriptomics and proteomics show that there are significant differences in RNA transcription and protein expression between single cells and cell populations. As an organic macromolecule, protein is the material basis of life, the basic organic matter constituting cells, and the main undertaker of life activities. Moreover, epigenetic modifications such as acetylation, ubiquitination, and phosphorylation play a crucial role in the regulation of protein functions. The genome and transcriptome research cannot meet the needs of human beings to explore the heterogeneity in the occurrence and development of diseases.

However, existing technical means cannot meet the requirements of circulating tumor cell detection at the protein expression level. Fluorescence flow cytometry and mass cytometry newly developed nowadays are widely used in the study of cell heterogeneity. However, the methods require a large sample size and cannot detect trace cell samples such as circulating tumor cell. The IsoLight single-cell function information multiplexing detection system of IsoPlexis is currently the most cutting-edge and indispensable solution in the field of single-cell analysis, which can provide complete cell function response analysis at the single-cell resolution and sensitivity. However, the system can only detect cell secretory proteins, and cannot monitor the characteristics related to a functional status on a cell surface and inside a cell. Western blotting is a protein determination method commonly used in the cell and molecular biology and the immunogenetics. Specifically, a protein in a sample is separated through gel electrophoresis, then transferred to a membrane (nitrocellulose or PVDF), and detected with an antibody specific to a target protein. Since the protein is separated by electrophoresis and then subjected to antibody conjugation, the antibody cross-reactivity leads to little impact on the detection. Therefore, even in a complex sample such as a cell lysate, an on-target signal can be clearly distinguished from an off-target signal. However, results obtained by traditional western blotting are based on an average protein expression level for a large number of cell samples, which ignore the specificity and diversity of protein expression in single cells. The cell immunofluorescence technology also plays an indispensable role in the study on CTC heterogeneity, but is highly doubted by scientists due to non-specific staining and antibody cross-reactivity.

It has been proved that the above technologies are very important for the separation of circulating tumor cells and the analysis of significant differences in single-cell protein expression, but all have disadvantages.

The separation and analytical separator of circulating tumor cells still stagnates at counting or sequencing analysis, with little analysis at the protein level, and the analysis often relies on large instruments.

In existing circulating tumor cell separation techniques such as the immunomagnetic bead method, a sample needs to be incubated with immunomagnetic beads, which requires a long period and affects the subsequent analysis and research on cells.

Existing circulating tumor cell analysis techniques such as cellResearch still stagnate at the counting level. Due to the small quantity of CTCs, fluorescence flow cytometry, mass cytometry, and the like cannot be used. However, cell immunofluorescence counting has high requirements on the quality and quantity of antibody probes, and sometimes it may be impossible to find an antibody probe that corresponds to a target and meets compound detection requirements, which greatly limits the application of this method. The single-cell secretory protein detection technology can only detect secretory proteins, but cannot detect cell surface proteins, transmembrane proteins, intracellular proteins, and nuclear proteins.

The microfluidic technology has the advantages of low sample and reagent consumption, structure and function diversity, high integration degree, and the like. However, some chips require a complicated manufacture process, and are difficult to control single-cell separation and detection. If a material used for the chip manufacture has insufficient biocompatibility, the cell function characterization may be changed, such that an obtained result cannot reflect the true situation of the true life activity state of the human body.

Therefore, in order to fully understand the heterogeneous behaviors of individual cells in a complex cell population, those skilled in the art are committed to developing a new single-cell protein expression analysis technology for circulating tumor cells.

SUMMARY OF THE INVENTION

In view of the above-mentioned shortcomings in the prior art, a technical problem to be solved by this application is to provide a fast, sensitive, and stable microfluidic chip, and a new single-cell western blotting technology using the microfluidic chip, which provides a new method for single-cell protein quantitative analysis, single-cell omics, and cell heterogeneity research.

To achieve the above objective, this application provides a microfluidic chip, including: a first unit which includes a channel for a cell sample to pass through and is configured to separate circulating tumor cells in the cell sample;

a second unit, a front end of which communicates with a tail end of the first unit, and the second unit is configured to capture single cells from the separated circulating tumor cells and subject the captured single cells to closed lysis; and a gel layer which is provided at the second unit;

where the microfluidic chip is configured to implement the binding of a protein molecule of the single cell with an antibody in the gel layer after the single cell is lysed.

Further, the microfluidic chip further includes a filter membrane arranged at the tail end of the first unit.

Further, the channel includes at least one arc portion.

Further, the channel includes a first channel, and the first channel is a serpentine channel.

Further, the channel further includes a second channel in communication with the first channel, and a diameter of the second channel gradually increases in a direction from the first channel to the second unit.

Further, the second unit includes at least one well formed in the gel layer, and the well is configured to accommodate the single cells.

Further, a buffer that induces the lysis of the single cells is provided in the well.

Further, the second unit includes a plurality of wells uniformly distributed.

Further, the microfluidic chip is further configured to use an electric field to separate the protein molecule of the single cell through electrophoresis after the single cell is lysed, and implement the binding of the separated protein molecule with the antibody.

Further, the microfluidic chip further includes:
a basal layer;
a second interlayer which is provided on the basal layer, and the second unit is provided on the second interlayer; and
a first interlayer which is provided on the second interlayer, and the first unit is provided on the first interlayer.

Further, the second unit includes a second hole provided on the second interlayer, and the gel layer is located in the second hole.

Further, the first interlayer includes a first hole provided at the tail end of the first unit, and the first hole communicates with the channel and is aligned with the second hole.

Further, the first interlayer and the second interlayer are both made of polydimethylsiloxane.

This application also provides a cell separation and single-cell western blotting method using the microfluidic chip described above, including the following steps:
(a) introducing a pretreated cell sample into the first unit of the microfluidic chip to obtain separated circulating tumor cells;
(b) capturing the separated circulating tumor cells;
(c) lysing the captured circulating tumor cells; and
(d) implementing the binding of a circulating tumor cell lysate with an antibody.

Further, the method further includes: (c1) before the binding of the circulating tumor cell lysate with the antibody, applying an electric field on the microfluidic chip, such that a protein molecule of the circulating tumor cell is separated through electrophoresis.

Further, the method further includes: (c2) in situ immobilizing the separated protein molecule under light.

Further, the step of implementing the binding of a circulating tumor cell lysate with an antibody includes:
incubating a primary antibody capable of recognizing the protein molecule of the circulating tumor cell; and
allowing a secondary antibody with a luminescent label to recognize the primary antibody.

Further, after the binding of the circulating tumor cell lysate with the antibody, the microfluidic chip is placed in an observation device to determine a light signal intensity of the protein molecule.

Further, the method further includes: (a1) filtering the separated circulating tumor cells. This application also provides a manufacture method of the microfluidic chip described above, including:
preparing a polydimethylsiloxane mixed colloid;
placing the polydimethylsiloxane mixed colloid on a silicon wafer with a preset pattern to form a first interlayer with a channel;
forming a first hole on the first interlayer;
coating the polydimethylsiloxane mixed colloid on a basal layer to form a second interlayer, and forming a second hole on the second interlayer;
filling the second hole with a gel, and placing a silicon wafer mold with a cylinder array on the gel inversely to form a gel with a microhole array; and
bonding the first interlayer with the channel and the second interlayer comprising the gel with the microhole array together.

The microfluidic chip and the cell separation and western blotting method using the microfluidic chip proposed in this application have the following technical effects:
1. Compared with the prior art, this application only uses the fluid mechanics to realize the label-free, high-throughput, and high-purity separation of circulating tumor cells from white blood cells in the microfluidic chip; and a sample does not require complicated treatment, the throughput, speed, and separation rate are high, and no additional work field is required.
2. After the separation, the cell activity is not affected, and intact cells can be obtained, which provides a favorable means for later research. The design of the filter membrane is used to realize the further purification and concentration of the separated CTCs, which is convenient for the subsequent analysis of the collected CTCs.
3. The light-sensitive in situ immobilized single-cell western blotting is introduced, and the integration of the separation and analysis of circulating tumor cells on a single chip is proposed for the first time.
4. An expression level of a target protein in a single circulating tumor cell can be quantitatively analyzed, and single-cell western blotting analysis can be performed on multiple circulating tumor cells at the same time.

The concept, specific structures, and technical effects of this application will be further described below in conjunction with accompanying drawings, such that the purpose, features, and effects of this application can be fully understood.

DETAILED DESCRIPTION OF THE PREFERRED EMBODIMENTS

Figure 1:
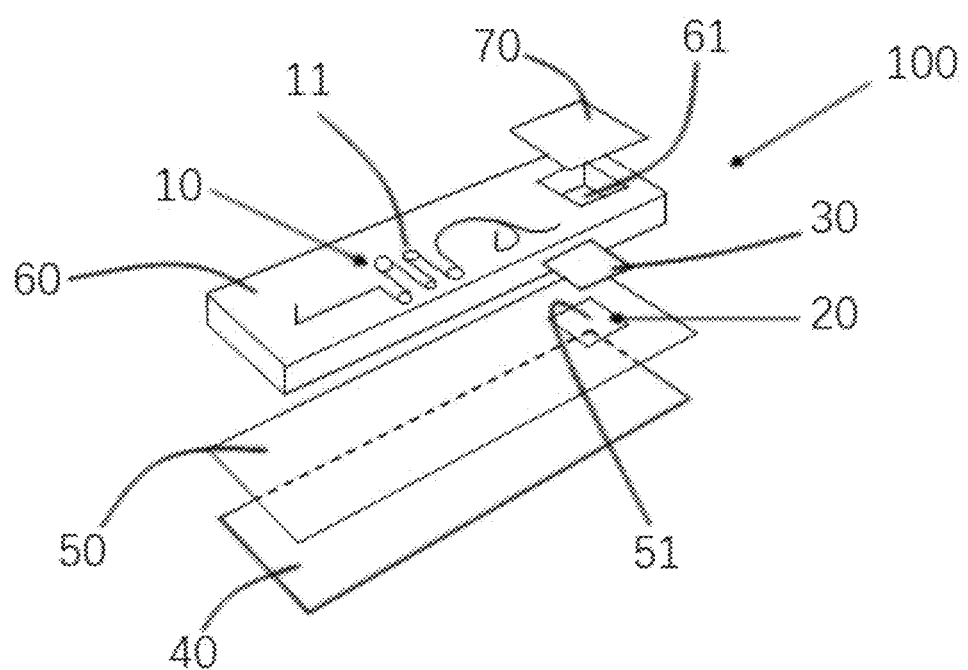
FIG. 1 is a schematic exploded view of a microfluidic chip of a preferred example according to this application.

A number of preferred examples of this application will be introduced below with reference to the accompanying drawings of the specification, such that the technical content can be clearly and easily understood. This application can be embodied through examples of many different forms, and the protection scope of this application is not limited to the examples mentioned herein.

In the drawings, components with the same structure are denoted by the same numeral, and components with similar structures or functions are denoted by similar numerals. The size and thickness of each component are randomly shown in the drawings, and this application does not limit the size and thickness of each component. In order to make the illustration clearer, a thickness of a component is appropriately exaggerated in some places of the drawings.

The PDMS mentioned in this application refers to polydimethylsiloxane.

Example 1

Figure 2:
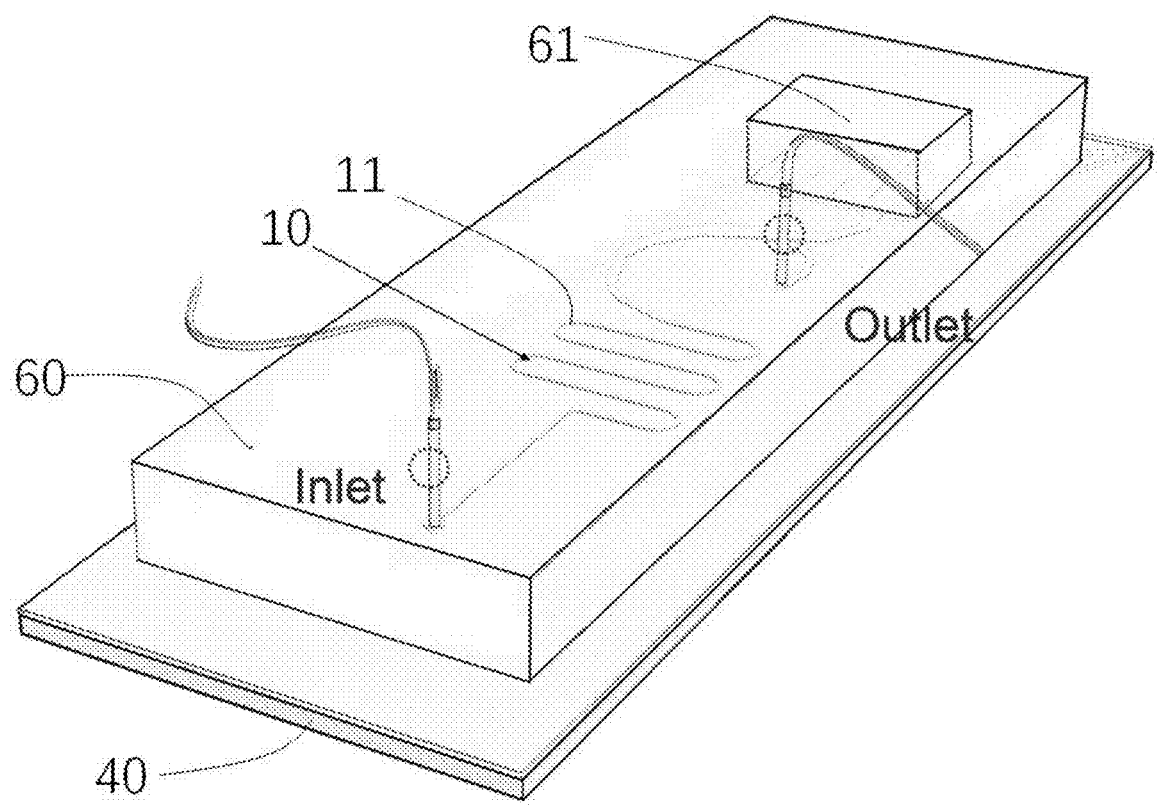
FIG. 2 is a schematic structural diagram of a microfluidic chip of a preferred example according to this application.

As shown in FIG. 1 and FIG. 2, the microfluidic chip 100 provided by this application includes: a circulating tumor cell separation unit 10, which has a channel 11 for a cell sample to pass through and can rapidly separate circulating tumor cells from a complex cell sample; a single-cell capture unit 20, a front end of which communicates with a tail end of the circulating tumor cell separation unit 10, and the single-cell capture unit can capture single cells from separated and enriched target cells and further subject the captured single cells to closed lysis; and a gel layer 30 which is arranged at the single-cell capture unit 20, where the single-cell western blotting analysis can be completed on the gel layer 30.

The microfluidic chip 100 proposed in this application is a fast, sensitive, and stable chip to realize label-free high-throughput separation and single-cell western blotting analysis of circulating tumor cells. This application combines the microfluidic chip 100 and the western blotting technology, that is, through the structural design of the microfluidic chip 100, the cell separation and single-cell western blotting technologies are integrated on the microfluidic chip 100, which fundamentally solves the problems of cell number limitation, slow analysis speed, low detection sensitivity, and the like in the circulating tumor cell separation on a microchip and single-cell western blotting.

Figure 3:
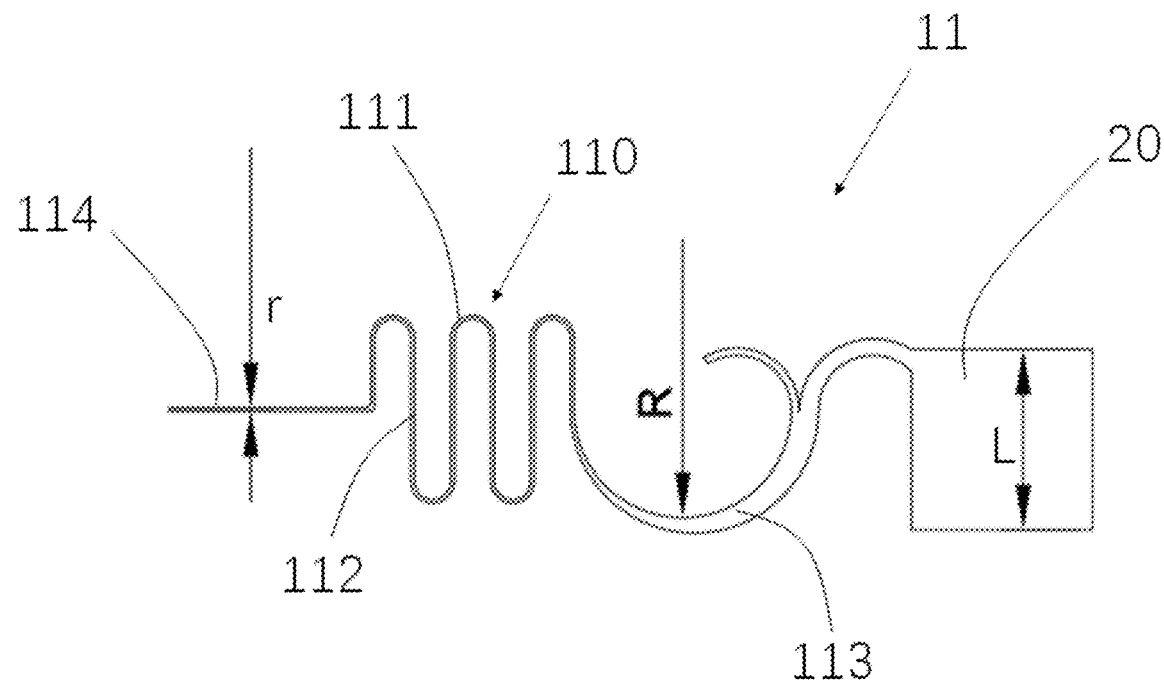
FIG. 3 is a schematic diagram of a channel of a preferred example according to this application.
Figure 4:
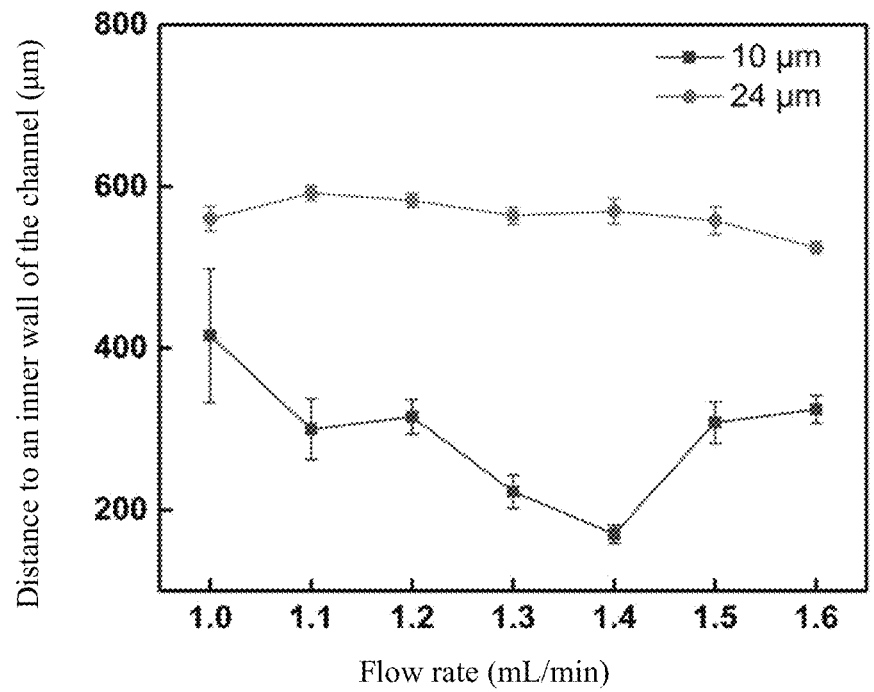
FIG. 4 is a diagram showing a relationship of a flow rate with a distance between equilibrium positions of circulating tumor cell and white blood cell in a channel of a separation unit.
Figure 5:
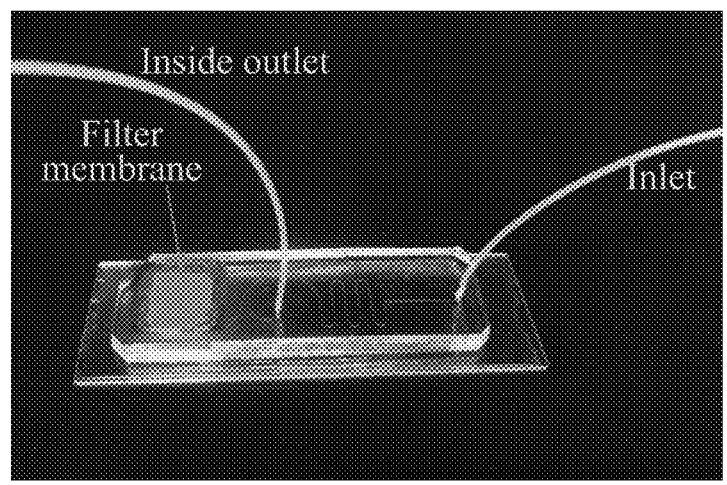
FIG. 5 is a physical picture of a microfluidic chip of a preferred example according to this application.
Figure 6:
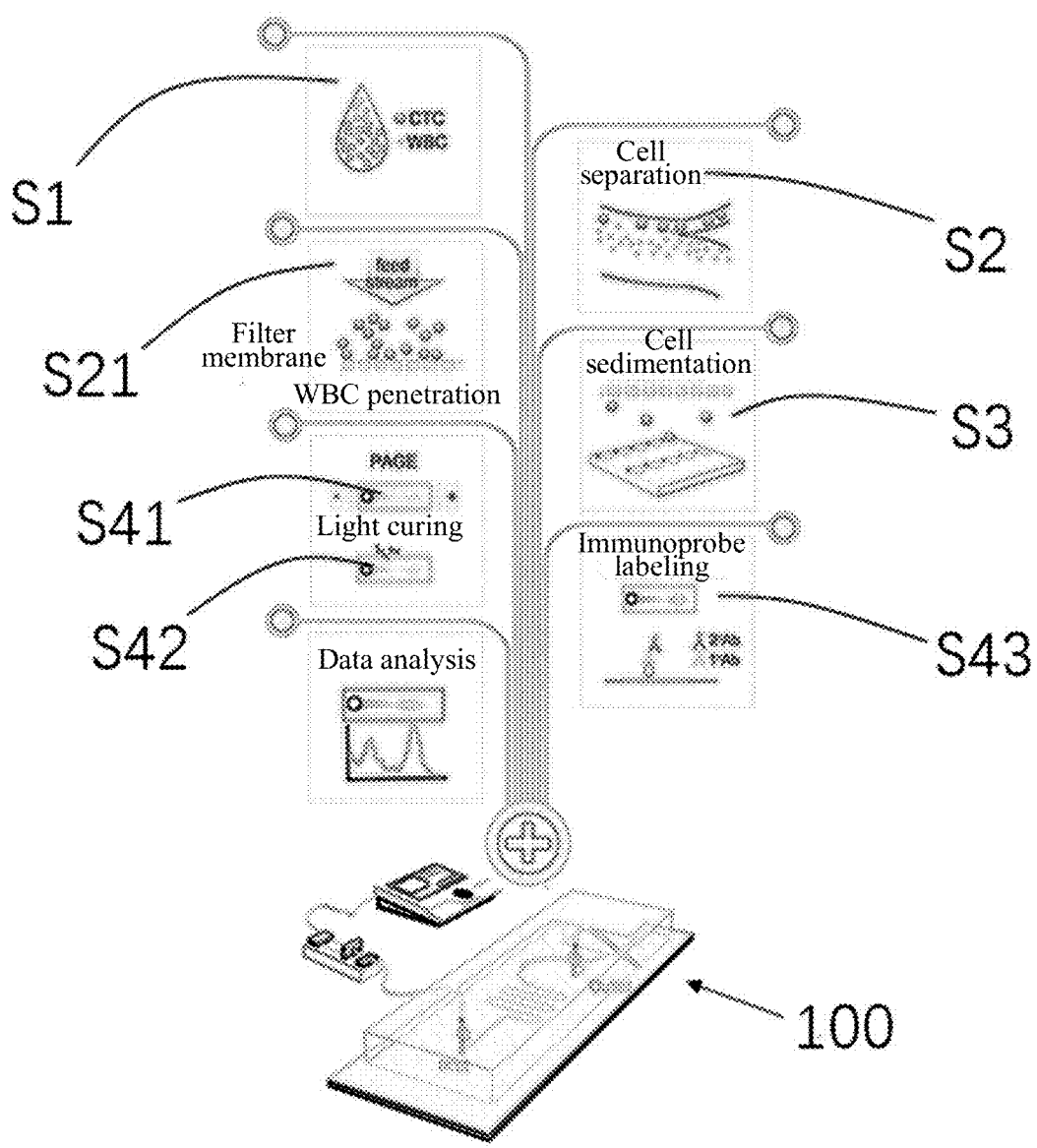
FIG. 6 is a schematic design diagram of a preferred example according to this application.
Figure 7:
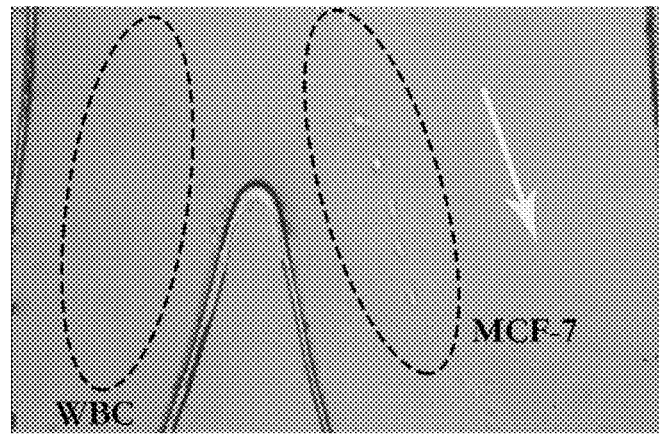
FIG. 7 is a screenshot of cell distribution in a channel when a microfluidic chip is performing cell separation according to a preferred example of this application.

The circulating tumor cell separation unit 10 is provided to separate circulating tumor cells from a cell sample. In the channel 11 of the circulating tumor cell separation unit, circulating tumor cells and white blood cells are under different stresses in the channel 11 due to different sizes and thus separated. Specifically, the properties of a fluid at a microscale and the different sizes of circulating tumor cells and white blood cells enable the separation of circulating tumor cells and white blood cells. At a microscale, when the Reynolds number of the microfluidic chip 100 is less than 2,300, a fluid in the microfluidic chip 100 forms a laminar flow, and particles with different sizes occupy different equilibrium positions in the laminar flow due to the equilibrium of inertial force and Dean's drag force. In some implementations, the channel 11 has at least one arc portion 111, and when a cell sample passes through the arc portion 111, particles with different sizes are separated due to different stresses. In some implementations, the channel 11 includes a serpentine channel 110, which is formed by connecting a plurality of linear portions 112 and arc portions 111 in sequence. In some implementations, the channel 11 can also be arranged as a spiral channel or a channel with another irregular shape and an arc portion. In some implementations, the channel 11 also includes a semicircular channel 113 in communication with the serpentine channel 110, and a diameter of the semicircular channel 113 gradually increases in a direction from the serpentine channel 110 to the single-cell capture unit 20, such that separated cells can leave the channel 11; and a radius R of the semicircular channel 113 can be set according to actual requirements, and as shown in FIG. 3, the radius R is 6 mm. In some implementations, the separation unit 10 further includes a drainage channel 114, which is arranged in front of the arc portion 111 of the channel 11 to drain a cell sample from the outside into the channel 11. As shown in FIG. 3, according to different circulating tumor cell sizes, various portions of the channel 11 and the drainage channel 114 can have different diameters. For example, the drainage channel 114 and the serpentine channel 110 can have the same diameter r of 0.2 mm.

With the separation of breast cancer cell line MCF-7 (with a diameter of about 22 μm to 28 μm) from white blood cells (with a diameter of about 8 μm to 18 μm) as an example, as shown in the figure, when a flow rate is set to 1.4 mL/min, the maximum separation distance can be achieved for the two. The flow rate can be adjusted and optimized according to circulating tumor cells with different sizes. In this application, a sample only needs to be subjected to conventional red blood cell lysis, and then a resulting supernatant is removed. Compared with other existing technologies, this application reduces the time for incubating cells with immunomagnetic beads and reduces the cost. The process has high throughput, a short separation time at a sample flow rate of 1.4 mL/min, and a separation rate of higher than 68%. Moreover, in the entire separation process, no work field (such as electric field and magnetic field) needs to be applied additionally, there is no need to modify cells (such as incubation with immunomagnetic beads), and cells flowing through the chip 100 have unaffected activity and are intact.

The single-cell capture unit 20 can capture single cells from separated and enriched cells and subject captured cells to closed lysis. After passing through the separation unit 10, a cell sample enters the single-cell capture unit 20. The single-cell capture unit 20 can capture single circulating tumor cells. Specifically, a gel layer 30 is provided at the single-cell capture unit 20, and a cell well 21 is formed on the gel layer 30. The cell well 21 is a hole-shaped structure formed on the gel layer 30, and a diameter of the cell well is adapted to a size of circulating tumor cells. After entering the gel layer 30, circulating tumor cells flow with a liquid and sink into the cell well 21, such that a single circulating tumor cell enters a hole, thereby achieving the capture of single cells. In some implementations, there can be a plurality of cell wells 21, and preferably, the plurality of cell wells 21 form a microhole array and are uniformly distributed, such that a plurality of circulating tumor cells can be captured. A diameter of the cell well 21 can be adjusted according to a size of circulating tumor cells to be separated. For example, for the analysis of breast cancer circulating tumor cells (with a diameter of about 22 μm to 28 μm), a cell well 21 with a diameter of 30 μm is adopted to ensure that a single cell can enter the hole. After a cell enters the hole, a single-cell lysis buffer preheated to 55° C. can be added to achieve the lysis of the captured single cell. It should be understood that different lysis buffers can be used for different circulating tumor cells, and the preheating temperature can also be set according to actual needs.

In some implementations, the microfluidic chip 100 further includes a filter membrane 70, which is arranged at a tail end of the separation unit 10 to further purify and concentrate a separated cell cluster. After passing through the separation unit 10, a cell sample is filtered through the filter membrane 70 to remove white blood cells with a particle size smaller than a pore size of the filter membrane 70 and excess buffer. The pore size of the filter membrane 70 can be adjusted according to a size of circulating tumor cells to be separated. For example, for the separation of breast cancer circulating tumor cells (with a diameter of about 22 μm to 28 μm), a filter membrane pore size of 20 μm can be adopted. When a liquid just enters the chip 100, it takes a specified time to stabilize the fluid, and thus some white blood cells will appear at an outlet of circulating tumor cells. Therefore, a filter membrane 70 is pasted on the outlet of circulating tumor cells to further purify circulating tumor cells, thereby eliminating the influence of background cells.

Circulating tumor cells, after being captured by the single-cell capture unit 20, can be subjected to western blotting analysis. In some implementations, after the circulating tumor cells are captured and lysed by the single-cell capture unit 20, a resulting cell lysate can be directly recognized by and bound with a specific primary antibody and a secondary antibody labeled with a fluorescent or luminescent group, and then an observation device such as a laser confocal fluorescence microscope is used to determine a fluorescence signal intensity of the target protein molecule. In some implementations, after the circulating tumor cells are captured and lysed by the single-cell capture unit 20, an electric field is applied to the microfluidic chip 100. For example, the microfluidic chip 100 can be placed in a device capable of generating an electric field, such that a protein enters the gel layer 30 of the chip 100 under the action of the electric field to start electrophoretic separation. After the electrophoresis is over, the surface of the gel is irradiated with excitation light of a specified wavelength and intensity to achieve the in situ polymerization of the protein molecule and the gel monomer molecule in a protein band of the gel coating. Then the western blotting analysis is conducted, where an immobilized protein molecule is recognized by and bound with a specific primary antibody and a secondary antibody labeled with a fluorescent or luminescent group, and a laser confocal fluorescence microscope is used to determine a fluorescence signal intensity of the target protein molecule. For the light-sensitive immobilization and western blotting analysis of a protein, the Chinese Patent No. CN112390763A is incorporated herein by reference in its entirety.

In some implementations, the microfluidic chip 100 has a multilayer structure, and the circulating tumor cell separation unit 10 and the single-cell capture unit 20 may be arranged in different layers. Specifically, the microfluidic chip 100 includes a basal layer 40, a second interlayer 50 arranged on the basal layer 40, and a first interlayer 60 arranged on the second interlayer 50, where the circulating tumor cell separation unit 10 is arranged on the first interlayer 60 and the single-cell capture unit 20 is arranged on the second interlayer 50. During a manufacture process, the circulating tumor cell separation unit 10 is formed on the first interlayer 60 according to a preset pattern of the channel 11; a tail end of the separation unit 10 is provided with a first hole 61 that penetrates through the first interlayer 60 in a thickness direction of the first interlayer 60, and the first hole 61 communicates with the channel 11; and a second hole 51 is provided on the second interlayer 50 at a position corresponding to the first hole 61, and a gel layer 30 with a structure of the cell well 21 is provided in the second hole 51. Preferably, the filter membrane 70 covers a side of the first hole 61 facing towards the second interlayer 50. The first hole 61 and the second hole 51 can be square, and a side length can be set according to actual requirements, for example, the side length is set to 10 mm in the figure.

In some implementations, an inlet and an outlet of the channel 11 may each be connected with a conduit, where the conduit at the inlet is provided to introduce a cell sample and the conduit at the outlet is provided to draw out excess liquid.

Example 2

This application provides a method for analyzing circulating tumor cells using the microfluidic chip 100, where the separation and western blotting analysis of circulating tumor cells are integrated on the microfluidic chip 100, which improves the analysis efficiency and accuracy, and provides a new method for single-cell protein quantitative analysis, single-cell omics, and cell heterogeneity research.

A basic process of the method of this application is as follows:

Step S1: Pretreatment of a blood sample. This step can be conducted by any method known in the art, which does not limit this application. In some implementations, a blood sample is subjected to red blood cell lysis, then centrifuged, and diluted and suspended with a large volume of PBS or normal saline.

Step S2: A pretreated cell sample is introduced into the circulating tumor cell separation unit 10 of the microfluidic chip 100 to complete the separation and enrichment of the target cell. Due to the channel 11 of the separation unit 10, the circulating tumor cells and white blood cells can be separated by using the principle that they are different in size and are under different stresses in the microfluidic channel 11.

Step S3: Single cells are captured from the separated cells and then lysed. A target cell exiting the channel 11 enters the single-cell capture unit 20 of the microfluidic chip 100 and is further introduced into the cell well 21, such that a circulating tumor cell enters a cell well 21. When a plurality of cell wells 21 are provided, a plurality of circulating tumor cells can be captured at the same time. A captured circulating tumor cell is lysed through the lysis buffer in the cell well 21.

Step S4: A circulating tumor cell lysate is subjected to western blotting analysis.

In some implementations, in order to further purify and concentrate circulating tumor cells, after step S2, step S21 can be added to filter a separated cell solution: a filter membrane 70 is added to remove white blood cells smaller than pores of the filter membrane 70 and excess buffer, thereby eliminating the influence of background cells.

The step S2, step S3, and step S4 are all completed on the microfluidic chip 100, and the filtration step S21 is also completed on the microfluidic chip 100.

Using different western blotting analysis methods, step S4 can also include different operations. In some implementations, a target protein of circulating tumor cell obtained after lysis directly bind to a specific antibody and then is subjected to staining and destaining, and different fluorescence intensities of different proteins are determined by an observation device, where the observation device can be a laser confocal fluorescence microscope, a fluorescence scanning array system, or the like. In some implementations, step S4 further includes:

S41: An electric field (for example, 40 V/min) is applied on the microfluidic chip 100 to achieve electrophoretic separation. The electric field can be applied by any means known in the art. After the electric field is applied, the protein in the circulating tumor cells enter the gel layer 30 under the action of the electric field to start electrophoretic separation.

S42: Light-sensitive immobilization of protein. After the gel electrophoresis is over, the surface of the gel is irradiated with excitation light of a specified wavelength and intensity to achieve the in situ polymerization of the protein molecule and the gel monomer molecule in a protein band of the gel layer 30.

S43: Western blotting analysis. Then an immobilized protein molecule is recognized by and bound with a specific primary antibody and a secondary antibody labeled with a fluorescent or luminescent group, and an observation device is used to determine a fluorescence signal intensity of the target protein molecule.

Example 3

The breast cancer cell line MCF-7 cells are used to simulate circulating tumor cells in a breast cancer patient, and MCF-7 cells are mixed into normal human blood to simulate a blood sample collected from a breast cancer patient to verify the function of the microfluidic chip 100.

Figure 8:
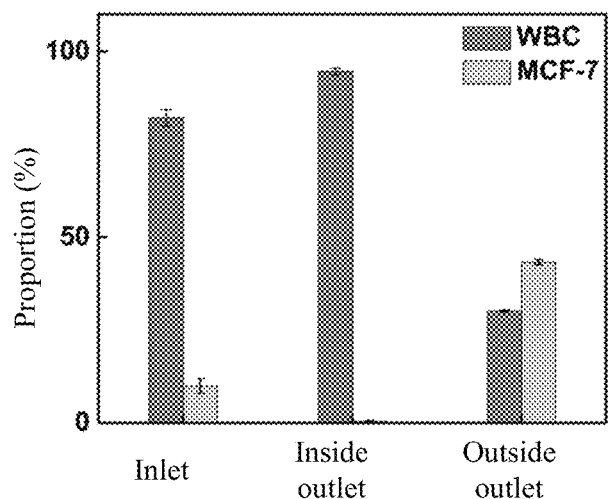
FIG. 8 is a diagram showing the CTC separation effect of a microfluidic chip of a preferred example according to this application.
Figure 9:
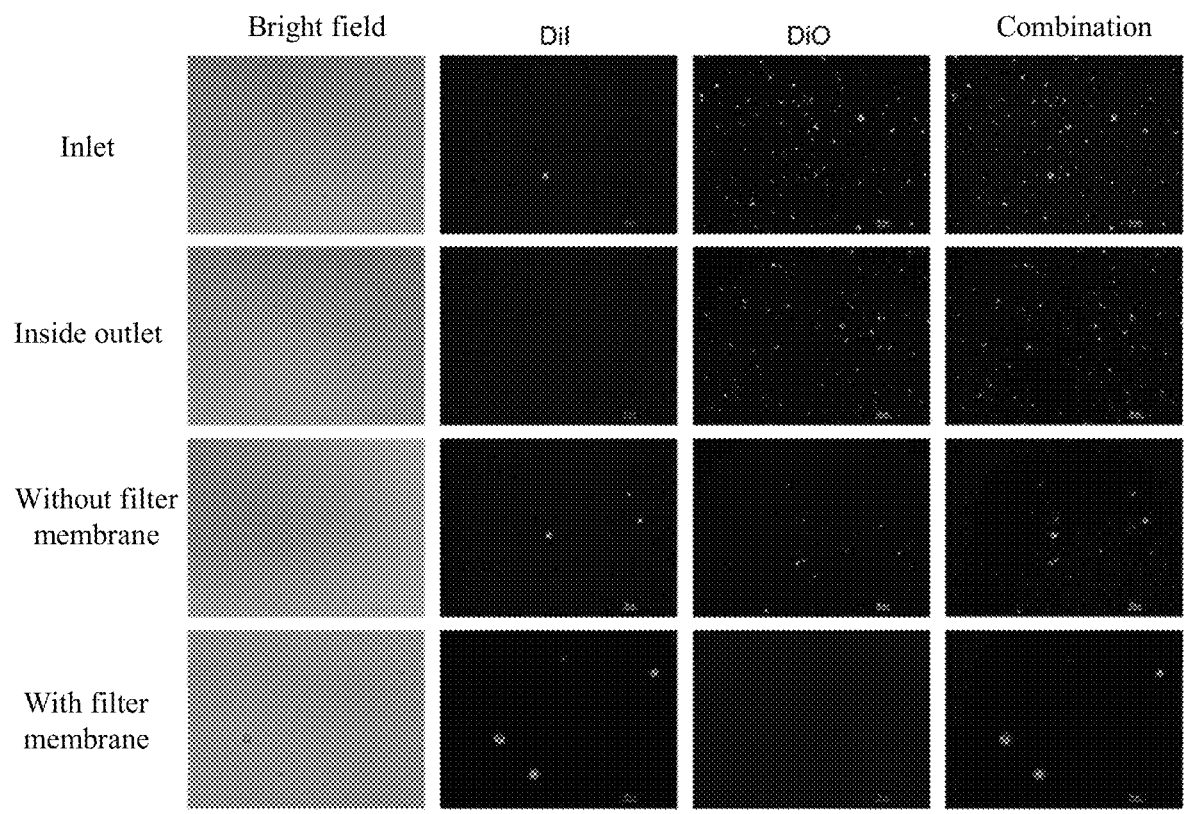
FIG. 9 is a diagram showing the purity of circulating tumor cells after filtration, concentration, and purification by a filter membrane according to a preferred example of this application.
Figure 10:
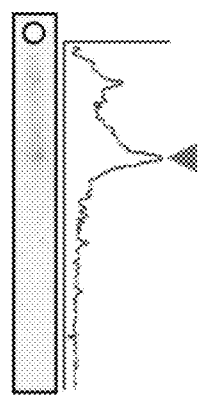
FIG. 10 is a fluorescence image for circulating tumor cells obtained through capture by a cell well, in situ lysis, electrophoresis, ultraviolet irradiation to immobilize a protein, and primary antibody and secondary antibody recognition according to a preferred example of this application.
Figure 11:
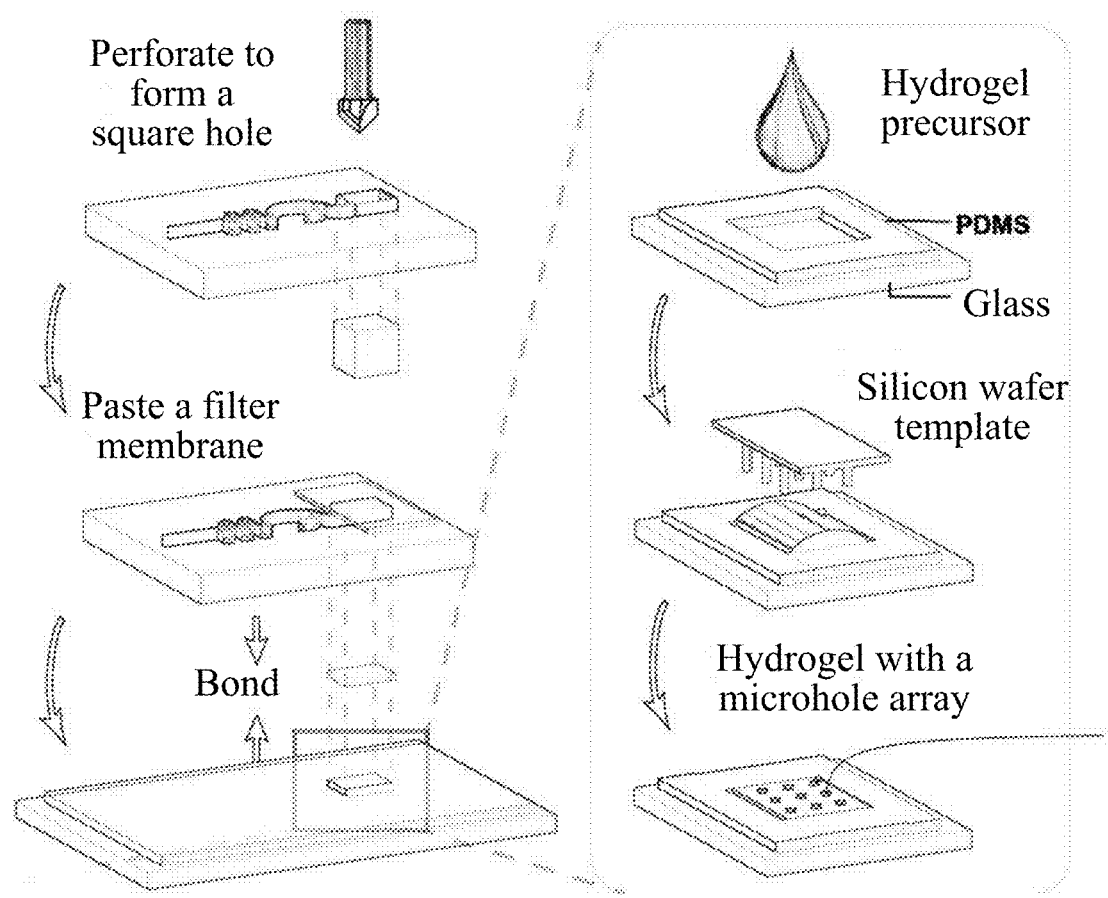
FIG. 11 is a manufacture flow chart of a microfluidic chip of a preferred example according to this application.

A screenshot of cell distribution in the separation channel 11 when MCF-7 cells are passing through the separation unit 10 of the microfluidic chip 100 is shown in FIG. 8. FIG. 9 shows the separation effect, where a separation efficiency of MCF-7 is 68% and a purity is 96%. As shown in FIG. 10, MCF-7 cells show a higher purity after being filtered, concentrated, and purified by the filter membrane 70. As shown in FIG. 11, circulating tumor cells are captured by the cell well 21, then subjected to in situ lysis and electrophoresis, then irradiated with ultraviolet light to immobilize a protein, and recognized by a primary antibody and a secondary antibody, and a fluorescence image and data processing results show that the protein analysis at the single-cell level is achieved on the separated circulating tumor cells.

Example 4

A manufacture method of the microfluidic chip 100 is provided in this example, specifically as follows:

Step S100: Preparation of a polydimethylsiloxane (PDMS) mixed colloid. An appropriate amount of polydimethylsiloxane and an appropriate amount of polydimethylsiloxane curing agent are weighed, added to a container successively, and then thoroughly stirred to remove bubbles in the mixed colloid. A ratio of the polydimethylsiloxane to the polydimethylsiloxane curing agent is 12:1 to 8:1. The stirring can be conducted with a glass rod. In some implementations, vacuum-pumping can be conducted in a vacuum environment to ensure that there are no bubbles in the mixed colloid. Other methods can also be used to remove bubbles. Preferably, the preparation process is conducted in a clean room environment.

Step S200: Manufacture of a first interlayer 60 with a separation unit 10. The mixed colloid undergoing vacuum-pumping is introduced into a petri dish in which a silicon wafer with a target pattern (the target pattern corresponds to a shape of a channel 11 of the separation unit 10), such that the mixed colloid covers a surface of the silicon wafer; and the mixed colloid is dried, and a formed first interlayer 60 is removed from the silicon wafer. In some implementations, after the mixed colloid covers the silicon wafer, bubbles between the silicon wafer and the petri dish can be removed before the drying operation. During a drying process, the flatness of the first interlayer 60 should be ensured to prevent an experimental result from being affected. Specifically, vacuum-pumping is conducted such that there are no bubbles between the silicon wafer and a bottom of the petri dish; the petri dish is dried in an electrothermal constant-temperature drying box; a shelf in the drying box must be horizontal, otherwise, the first interlayer 60 obtained after the drying is uneven, which will affect an experimental result to some extent; and then the petri dish is taken out, the first interlayer 60 is slowly peeled off from a surface of the silicon wafer with a utility knife, and the patterned part is cut into a square, and then perforated to form an inlet and an outlet. The following three points should be noted in this step: 1. In a process of peeling off the first interlayer 60, a utility knife should not touch the silicon wafer, otherwise, the silicon wafer will be broken. 2. During perforation, a corresponding inlet or outlet position on the channel 11 must be aligned, and it should be ensured that a perforator is vertically inserted into the first interlayer 60. 3. After the perforation is completed, an formed inlet or outlet needs to be poked with a fine wire to remove excess PDMS in the inlet or outlet. Four sides of a rectangular groove are cut through with a utility knife to form a rectangular frame with two transparent sides, which is the first hole 61.

Step S300: Paste of a filter membrane 70. The filter membrane is pasted on the rectangular frame at a side without the channel 11, and then a glue is dried. Before the paste, the filter membrane can be soaked in BSA and then dried. If the filter membrane 70 is not required, this step can be omitted.

Step S400: Manufacture of a second interlayer 50. A PDMS mixed colloid is prepared (the same as in step 100), and then coated on the basal layer 40. The basal layer 40 can be a glass sheet. Specifically, the PDMS mixed colloid can be coated by a spin-coater. That is, a PDMS mixed colloid layer with a thickness of 200 μm is spin-coated on a 75 mm×75 mm glass sheet by the spin-coater, and then dried in an oven. After the PDMS is peeled off, a rectangular frame (namely, the second hole 51) is cut at a corresponding position according to a size of the chip 100.

Step S500: Manufacture of a single-cell capture unit 20. The surfaces of the second interlayer 50 and the basal layer are cleaned with a transparent glue to ensure a clean surface, and then the second interlayer and the basal layer are cleaned in a plasma cleaning machine. The plasma cleaning machine is turned on, and a cleaning time is set to 50 s; vacuum-pumping is started, and a pressure in a chamber of the plasma cleaning machine is observed; when the pressure is reduced to a preset value, the vacuum-pumping is stopped, and a switch corresponding to the highest glow intensity is turned on; and when a purple glow appears in the chamber, timing is started. The second interlayer 50 and the glass slide are taken out and then immediately glued together. A rectangular or square groove on the basal layer with the second interlayer 50 is subjected to silanization for 0.5 h. An acrylamide gelatinization solution is added to the rectangular groove on the basal layer with the second interlayer 50 after the silanization, and a manufactured silicon wafer mold with a cylinder array is placed inversely on the rectangular groove. After the gelatinization, the mold is removed, and a gel with a microhole array is formed in the groove.

Step S600: Bonding of the first interlayer 60, the second interlayer 50 with the single-cell capture unit 20, and the basal layer. The first interlayer 60 and the basal layer treated in step S500 are bonded together through Plasma to obtain the microfluidic chip 100. Before the two are subjected to surface-plasma treatment, DI water can be added to the groove with hydrogel to prevent the hydrogel from being dried out during the large-area surface-plasma process. In order to further strengthen the bonding, the microfluidic chip 100 can be dried in an oven, during which a glue needs to be prevented from being dried out and turned up.

Step S700: Insertion of conduits. After the drying, a tetrafluoroethylene tube with an outer diameter of 0.8 mm is inserted into each of the inlet and outlet to avoid liquid leakage from the inlet and outlet during an experiment, and the inlet and outlet are sealed with a PDMS mixture.

Preferred specific examples of this application are described in detail above. It should be understood that, a person of ordinary skill in the art can make various modifications and variations according to the concept of this application without creative efforts. Therefore, all technical solutions that can be obtained by a person skilled in the art based on the prior art through logical analysis, deduction, or limited experiments according to the concept of this application should fall within the protection scope defined by the claims.

The invention claimed is:

1. A microfluidic chip, comprising:
   a first unit which comprises a channel for a cell sample to pass through and is configured to separate circulating tumor cells in the cell sample;
   a first interlayer, the first unit is provided on the first interlayer;
   a second interlayer, the first interlayer is provided on the second interlayer;
   a gel layer which is provided in the second interlayer; and
   a second unit, an inlet of which communicates with an outlet of the first unit, and the second unit is configured to capture single cells from the separated circulating tumor cells and subject the captured single cells to closed lysis; and the second unit is provided in the gel layer;
   wherein the microfluidic chip is configured to implement the binding of a protein molecule of a single cell with an antibody in the gel layer after the single cell is lysed.

2. The microfluidic chip of claim 1, wherein the microfluidic chip further comprises a filter membrane arranged at the outlet of the first unit.

3. The microfluidic chip of claim 1, wherein the channel comprises at least one arc portion.

4. The microfluidic chip of claim 3, wherein the channel comprises a first channel, and the first channel is a serpentine channel.

5. The microfluidic chip of claim 4, wherein the channel further comprises a second channel in communication with the first channel, and a diameter of the second channel gradually increases in a direction from the first channel to the second unit.

6. The microfluidic chip of claim 1, wherein the second unit comprises at least one well formed in the gel layer, and the at least one well is configured to accommodate the single cells.

7. The microfluidic chip of claim 6, wherein the second unit comprises a plurality of wells uniformly distributed.

8. The microfluidic chip of claim 1, further comprising a basal layer, the second interlayer is provided on the basal layer.

9. The microfluidic chip of claim 1, wherein a hole is provided in the second interlayer, and the gel layer is located in the hole.

10. The microfluidic chip of claim 1, wherein the first interlayer comprises a first hole provided at the outlet of the first unit, and the first hole communicates with the channel;
    a second hole is provided in the second interlayer, and the gel layer is located in the second hole; and
    the first hole is aligned with the second hole.

11. The microfluidic chip of claim 1, wherein the first interlayer and the second interlayer are both made of polydimethylsiloxane.

12. A cell separation and single-cell western blotting method using the microfluidic chip of claim 1, comprising the following steps:
    (a) introducing a pretreated cell sample into the first unit of the microfluidic chip to obtain separated circulating tumor cells;
    (b) capturing the separated circulating tumor cells;
    (c) lysing the captured circulating tumor cells; and
    (d) implementing the binding of a circulating tumor cell lysate with the antibody.

13. The method of claim 12, wherein the method further comprises: (c1) before the binding of the circulating tumor cell lysate with the antibody, applying an electric field on the microfluidic chip, such that a protein molecule of the circulating tumor cell lysate is separated through electrophoresis.

14. The method of claim 13, wherein the method further comprises: (c2) in situ immobilizing the separated protein molecule under light.

15. The method of claim 12, wherein the step of implementing the binding of a circulating tumor cell lysate with the antibody comprises:
    incubating a primary antibody capable of recognizing the protein molecule of the circulating tumor cell lysate; and
    allowing a secondary antibody with a luminescent label to recognize the primary antibody.

16. The method of claim 15, wherein after the binding of the circulating tumor cell lysate with the antibody, placing the microfluidic chip in an observation device to determine a light signal intensity of the protein molecule.

17. The method of claim 12, wherein the method further comprises: (a1) filtering the separated circulating tumor cells.

* * * * *